United States Patent [19]

Rocklage et al.

[11] Patent Number: 4,842,845
[45] Date of Patent: Jun. 27, 1989

[54] RADIOACTIVE METAL CHELATES FOR DIPYRIDOXYL PHOSPHATE

[75] Inventors: Scott M. Rocklage, Saratoga; Steven C. Quay, Los Altos Hills, both of Calif.

[73] Assignee: Salutar, Inc., Sunnyvale, Calif.

[21] Appl. No.: 47,616

[22] Filed: May 8, 1987

[51] Int. Cl.$^4$ .................. A61K 49/02; C07F 13/00
[52] U.S. Cl. ........................ 424/1.1; 534/10; 534/14
[58] Field of Search ............... 534/10, 14; 424/1.1

[56] References Cited

U.S. PATENT DOCUMENTS

3,981,980  9/1976  Baker et al. .................. 424/1.1

Primary Examiner—John S. Maples
Attorney, Agent, or Firm—William B. Walker

[57] ABSTRACT

Radioactive metal ion chelates of N,N'-bis-(pyridoxal-5-phosphate)-alkylenediamine-N,N'-diacetic acids, N,N'-bis-(pyridoxal-5-phosphate)-1,2-cycloalkylenediamine-N,N'-diacetic acids, and N,N'-bis-(pyridoxal-5-phosphate)-1,2-arylenediamine-N,N'-diacetic acids, the corresponding monophosphate compounds and monoacetic acid compounds, and their salts and esters form stable, highly soluble chelates with paramagnetic metal ions, and are highly effective agents for radiopharmaceutical imaging. Preferred contrast agents are radioactive metal ion such as technetium-99m and indium-111 ion chelates of N,N'-bis-(pyridoxal-5-phosphate)ethylenediamine-N,N'-diacetic acid, N,N'-bis-(pyridoxal-5-phosphate)trans-1,2-cyclohexylene-diamine-N,N'-diacetic acid, N,N'-bis-(pyridoxal-5-phosphate)trans-1,2-arylenediamine-N,N'-diacetic acid, and the soluble calcium salts thereof.

44 Claims, 1 Drawing Sheet

FIG._1.

RADIOACTIVE METAL CHELATES FOR DIPYRIDOXYL PHOSPHATE

FIELD OF THE INVENTION

This invention relates to novel, highly stable chelates with radioactive metal ions which are particularly useful as radiopharmaceuticals in medical imaging applications. In particular, this invention is directed to highly stable chelates of novel dipyridoxyl compounds with radioactive polyvalent metal ions, the preparation of these chelates, and the use of these chelates as radiopharmaceuticals in imaging.

BACKGROUND OF THE INVENTION

Traditionally, chelates have been used to administer poorly soluble salts in medicine and as antidotes for detoxification in cases of heavy metal or heavy metal isotope poisoning. Chelates with paramagnetic contrast agents have also been reported for use in NMRI methods.

Chelates have also been used to deliver radioisotopes to areas of the body for imaging and radiation therapy. Introducing radioactive metal ions into the body in the form of chelates is often advantageous, not only because stable chelated metal ions of toxic metals may be less toxic, but particular chelates have been found to increase the concentration of chelated radioactive metal ions in certain specific organs. To be useful in these applications, a chelate must be able to hold the radioactive metal ion tightly in the chelate structure, that is, the formation constant for the chelate must be very large at physiological pH. The radiochemical metal chelate must also be sufficiently soluble to permit administration of quantities required for imaging in reasonable volumes. Usual routes of administration are orally, intravenously and by enema.

The chelating agent must form a stable chelate with those radioactive metal ions which present a hazard to the body if released during use. The chelate forming agent (ligand) must be capable of forming a chelate with a selected radioactive metal ion without altering the metal's oxidation state or otherwise reducing its chemical stability.

This invention provides novel, superior chelates of radioactive metal ions which meet the above objectives.

DESCRIPTION OF THE PRIOR ART

Summaries of the history and state of the art of radiochemical metal reagents, including chelates of radioactive metal ions, are presented by Alazraki, N., et al, FUNDAMENTALS OF NUCLEAR MEDICINE. New York: The Society of Nuclear Medicine, Inc. (1984); THE CHEMISTRY OF RADIOPHARMACEUTICALS. Heindel, N. et al, Editors, Chicago: Masson Publishing (1978); and RADIOPHARMACEUTICALS: PROGRESS AND CLINICAL PERSPECTIVES. Fritzberg, A. Editor, Boca Raton: CRC Press (1986).

Chelates of N,N'-dipyridoxylethylenediamine-N,N'-diacetic acid (PLED) with $^{68}$Ga(III) and $^{111}$In(III) and their use as radiochemicals are described by Green, M. et al, *Int. J. Nucl. Med. Biol.* 12(5):381–386 (1985). Radiochemical chelates of a variety of other chelating compounds have been described in the literature. $^{99m}$Tc chelates of N-pyridoxyl-alpha-aminoacids are described in U.S. Pat. Nos. 4,440,739 and 4,489,053. Incorporating $^{99m}$Tc in red blood cells using pyridoxal or its salts, a stannous salt and an alpha-amino acid is described in U.S. Pat. No. 4,313,928.

$^{99m}$Tc, $^{113m}$In, $^{111}$In and $^{169}$Yb chelates of DTPA (diethylenetriaminopentaacetate) are described by Heindel, N. et al (supra, p 16). Heindel et al describe $^{99m}$Tc chelates of other chelating agents such as N-(2,6-dimethylphenylcarbamoylmethyl)iminodiacetic acid (HIDA), pyridoxylidene glutamate, pyridoxal-amino acid Schiff's bases (Heindel, N., et al, supra, p 20); of ethylenediaminetetracetic acid (EDTA), methyliminodiacetic acid (MIDA), citrate, gluconate, glucoheptonate, ascorbate, insulin, mannitol, dimercaptosuccinic acid, pyrophosphate, tetracycline, hydroxyethylidinediphosphate (HEDP), dihydrothioctic acid (DHTA) and isomercaptobutyric acid (Heindel, N., et al, supra, p 271); and of other iminodiacetic acid derivatives (IDA) such as p-carboxyphenylcarbamoylmethyliminodiacetic acid (CHIDA) and p-aminophenylcarbamoylmethyliminodiacetic acid (AHIDA) (Heindel, N., et al, supra, p 285).

The criterion for radionuclides most useful for imaging are described by Heindel, N., et al, (supra pp 36–38). The radioactive nuclide preferably possesses a gamma emission with an energy between about 20 and 600 KeV and a physical half-life of between approximately one hour and one year. For nuclides with multiple emissions, those above 600 KeV preferably represent less than 20 percent of total gamma emissions. Listed metal ions meeting these criterion are chromium-51, cobalt-57, gallium-67, indium-111, indium-113m, mercury-197, selenium-75, thallium-201, and technetium-99m. Other radiochemical metals disclosed by Heindel, N. et al (supra) are $^{203}$Pb, $^{85}$Sr, $^{87m}$Sr, $^{67}$Ga, $^{135m}$Sm, $^{153}$Sm and $^{171}$Er (p 15); $^{169}$Yb (p 16), $^{62}$Zn (p 28), $^{68}$Ga and $^{188}$Re (p 156); and radioactive isotopes of dysprosium and thulium (p 159).

U.S. Pat. No. 4,500,507 discloses kits and procedures for labeling porphyrin compounds with radioactive technetium isotopes, $^{99}$Tc, $^{95}$Tc and $^{99m}$Tc. Kits containing porphyrin and a stannous reducing agent to be used with a solution of the technetium isotope are described.

Use of alkylenediamine chelates with a variety of paramagnetic ions are described in U.S. Pat. No. 4,647,447. Ferrioxamine-paramagnetic contrast agents are described in U.S. Pat. No. 4,637,929. Paramagnetic metal ions complexed with polysaccharide derivatives of a variety of chelating compounds including EDTA, DTPA and aminoethyl diphosphonate are described in PCT application publication no. WO85/05554 (Application No. PCT/GB85/00234).

Taliaferro, C. et al in "New multidentate ligands. 22. N,N'-dipyridoxyethylenediamine-N,N'-diacetic acid: a new chelating ligand for trivalent metal ions", *Inorg. Chem.* 23:1188–1192 (1984) describes development of N,N'-dipyridoxyethylenediamine-N,N'-diacetic acid (PLED) as a chelating compound for trivalent metal ions. Other chelating compounds described are the Fe(III) chelates of N,N'-ethylenebis-2-(o-hydroxyphenyl)glycine (EHPG) and N,N'-bis(l-hydroxybenzyl)ethylenediamine-N,N'-diacetic acid (HBED). Properties of chelates of PLED, HBED, EHPG and EDTA with ions of copper, nickel, cobalt, zinc, iron, indium and gallium are compared. Taliaferro, C. et al, *Inorg. Chem.* 24:2408–2413 (1985) report their evaluation of PLED as a chelating ligand for the preparation of gallium and indium radiopharmaceuticals, and summarize properties of PLED chelates with Ga(III), In(III), and Fe(III).

U.S. Pat. No. 3,632,637 describes phenolic chelating agents such as N,N-di(o-hydroxylbenzyl)-ethylenediamine-N,N'-diacetic acid and their use in chelating trivalent and tetravalent metals.

SUMMARY OF THE INVENTION

The novel radiochemical complexes of this invention are complexes of radioactive multivalent metal ions with chelate forming compounds of this invention represented by Formula I.

wherein
R is hydrogen or $R_1$ is hydrogen or and one of R and $R_1$ is other than hydrogen;
$R_3$ is alkylene having from 1 to 8 carbons, 1,2-cycloalkylene having from 5 to 8 carbons, or 1,2-arylene having from 6 to 10 carbons, and
$R_4$ is hydrogen, alkyl having from 1 to 6 carbons or $R_5$ and $R_6$ are each, individually, hydroxy, alkoxy having from 1 to 18 carbons, hydroxy-substituted alkoxy having from 1 to 18 carbons, amino or alkylamido having from 1 to 18 carbons.

Chelates with phosphate group mono and diesters with mono and polyhydric alkanols having from 1 to 18 carbons, or alkylamino alcohols, each having from 1 to 8 carbons, and the salts of the above compounds are included within the scope of this invention.

Pharmaceutical compositions containing these chelates and their use in radiochemical imaging are also included within the scope of this invention.

DETAILED DESCRIPTION OF THE INVENTION

The chelates of this invention are chelates of polyvalent radioactive metal ions with the chelate forming compounds shown in Formula I. The compounds of Formula I, and salts, esters and chelates thereof with non-radioactive metal ions are the subject of our co-pending, concurrently filed application titled DIPYRIDOXYL PHOSPHATE NMRI CONTRAST AGENTS, Ser. No. 47,614, filed May 8, 1987, the entire contents of which are hereby incorporated by reference.

Chelates of the pharmaceutically acceptable water-soluble compatible salts and phosphate group esters of the compounds of Formula I with polyhydric alcohols, aliphatic alcohols, or alkylamino alcohols, each having from 1 to 18 carbons, are also included within the compounds of this invention.

In Formula I, $R_5$ and $R_6$ are preferably each individually hydroxy, alkoxy having from 1 to 8 carbons, ethylene glycol, glycerol, amino or alkylamido having from 1 to 8 carbons. Optimally, $R_5$ and $R_6$ are hydroxy and the salts thereof.

The term "alkyl" and "alkylene", as used herein, include both straight and branch-chained, saturated and unsaturated hydrocarbons. The term "1,2-cycloalkylene" includes both cis and trans cycloalkyl groups and alkyl substituted cycloalkylene groups bonded at the 1,2-positions to respective nitrogen atoms and alkyl substituted derivatives thereof having from 5 to 8 carbons. The term "1,2-arylene" includes phenyl and naphthyl groups bonded at the 1,2-positions to respective nitrogen atoms and alkyl substituted derivatives thereof, having from 6 to 10 carbons.

The compound, N,N'-bis-(pyridoxal-5-phosphate)-ethylenediamine-N,N'-diacetic acid or N,N'-bis(3-hydroxy-2-methyl-5-phosphonomethyl-4-pyridyl-methyl)ethylenediamine-N,N'-diacetic acid, is referred to hereinafter as DPDP, and the technetium-99m chelate is referred to hereinafter as Tc(DPDP).

The dicarbonyl compound of Formula I, when $R_5$ and $R_6$ are hydroxy and $R_3$ is ethylene, is DPDP. DPDP has the dissociation constants for the protonation sites shown in FIG. 1. As described in Example 8, at pH of 3 and above, the ligand is anionic and possesses deprotonated metal binding sites, both important criteria for metal chelating agents.

The chelates of this invention are radioactive polyvalent metal ion chelates of the compounds of Formula I. The chelates can be represented by Formulas II, III or IV.

-continued

In Formulas II, III and IV, Z represents a polyvalent, radioactive metal ion and $R_3$, $R_4$, $R_5$ and $R_6$ are the same as described with respect to the compounds of Formula I. The dotted lines in the figure represent the dative bonding between the oxygen and nitrogen atoms and the metal ion. One of the acetyl groups in Formula II is below the plane of the aromatic pyridine rings and the other acetyl group is above the plane of the aromatic pyridine rings, so the metal ion is tightly held within the interior of the chelate salt complex with the dicarboxy embodiments of this invention. Also included in the chelates of this invention are the pharmaceutically acceptable water-soluble compatible salts, and carboxylic and phosphate group esters with hydroxy-substituted alkanols, alkanols, or alkylamino alcohols, each having from 1 to 18 carbons, of the compounds of Formulas II, III, and IV.

For use as a medium for radiochemical imaging, the central cation of the complex chelate salt must be radioactive and have a valence which permits chelate formation, that is, a valence of from +1 to +5. It preferably emits a gamma emission with an energy between about 20 and 600 KeV and has a physical half-life of between approximately one hour and one year. For nuclides with multiple emissions, those above 600 KeV preferably represent less than 20 percent of total gamma emissions. The preferred cations are ions of chromium-51, cobalt-57, gallium-67, gallium-68, indium-111, indium-113m, mercury-197, selenium-75, thallium-201, technetium-95, technetium-99 and technetium-99m. However, radioactive metal ions of the chelates of this invention can include any other metal ions emitting alpha, beta, gamma, positron, or other radiation, including but not limited to metal ions of $^{203}$Pb, $^{85}$Sr, $^{87m}$Sr, $^{67}$Ga, $^{135m}$Sm, $^{153}$Sm, $^{171}$Er, $^{169}$Yb, $^{62}$Zn, $^{68}$Ga, and $^{186}$Re.

The preferred chelates of this invention are chelates of $^{99m}$Tc, $^{99}$Tc, $^{111}$In, $^{113m}$In, $^{67}$Ga, and $^{68}$Ga. Technetium-99m metal ion chelates having a valence of +1 to +5 are preferred.

The metastable isotope technetium-99m (Tc-99m) has a 6 hour half-life with a 99% gamma emission of 140 KeV, which is particularly well-suited for techniques of diagnostic nuclear medicine. Tc-99m has a high specific activity, $5.28 \times 10^9$ millicuries per gram (mCi/gm) and a convenient rapid rate of decay. The daughter product, Tc-99 has a specific activity which is 9 orders of magnitude lower and a half-life which is 8 orders of magnitude longer than Tc-99m. In recent years, Tc-99m has become readily available in hospitals through the use of selective elution from a molybdenum-99 (Mo-99) generator. The isotope Mo-99 (half-life of 67 hours) produces Tc-99m as a radioactive decay product (see for example, Jackson, et al, U.S. Pat. No. 4,031,198, the contents of which are hereby incorporated by reference).

For purposes of clarity, the chelates of this invention will be described hereinafter in terms of technetium-99m chelates. However, this is for purposes of clarity of explanation and not by way of limitation, and chelates of all radioactive metal ions are included within the scope of this invention.

If not all of the active hydrogen atoms of the chelates are substituted by the central radioactive metal ion, the solubility of the chelate is increased if the remaining hydrogen atoms are substituted with physiologically biocompatible cations of inorganic and/or organic bases or amino acids. For example, the lithium ion, the potassium ion, the sodium ion and especially the calcium ion are suitable inorganic cations. Suitable cations of organic bases include, for example, ethanolamine, diethanolamine, morpholine, glucamine, N,N-dimethylglucamine, N-methylglucamine. Lysine, arginine or orithine are suitable as cations of amino acids, as generally are those of other basic naturally occurring acids.

The preferred calcium salts have calcium ion to chelating molecule mole ratios of from 0.05 to 1.0, the optimum mole ratios being with the range of from 0.1 to 0.5. At mole ratios of calcium ion to chelate molecule above 1.0, the chelate tends to become insoluble. The soluble calcium salts are most physiologically acceptable since they do not significantly disturb the concentration of free calcium ions in the patient's system.

The chelates according to this invention are formed from the chelate forming compounds of Formula I by conventional procedures known in the art. In general, these processes involve dissolving or suspending the metal oxide or metal salt (for example, nitrate, chloride or sulfate) of the radioactive metal ion (for example, soluble oxides or salts of $^{99m}$Tc, $^{99}$Tc, $^{95}$Tc, $^{51}$Cr, $^{57}$Co, $^{67}$Ga, $^{68}$Ga, $^{111}$In, $^{113m}$In, $^{197}$Hg, $^{75}$Se, $^{201}$Tl, $^{203}$Pb, $^{85}$Sr, $^{87m}$Sr, $^{67}$Ga, $^{135m}$Sm, $^{153}$Sm, $^{171}$Er, $^{169}$Yb, $^{62}$Zn, and $^{186}$Re in water or a lower alcohol such as methanol, ethanol or isopropanol. To this solution or suspension is added an equimolar amount of the chelating acid in water or a lower alcohol, and the mixture is stirred, if necessary, with heating moderately or to the boiling point, until the reaction is completed. If the chelate salt formed is insoluble in the solvent used, the reaction product is isolated by filtering. If it is soluble, the radioactive reaction product is directly used for diagnostic imaging.

For making technetium-99m chelates, a reducing agent for pertechnetate Tc(VII) is required to allow coordination of the technetium to the chelating acid. Any reducing agent which can convert Tc(VII) into any lower valent technetium is usable provided it produces no material or harmful toxicity. Preferred reducing agents include any stannous salt, for example, stannous halides, stannous acetate, stannous citrate, stannous glucoheptanoate, and the like.

If acid groups such as the phosphoric acid groups are still present in the resulting chelate, it is advantageous to convert the acidic chelate salt into a neutral chelate salt by reaction with inorganic and/or organic bases or amino acids, which form physiologically biocompatible cations. This is often unavoidable since the dissociation of the chelate salt is moved toward neutrality to such an extent by a shift in the pH value during the preparation that only in this way is the isolation of homogeneous products or at least their purification made possible. Production is advantageously performed with organic bases or basic amino acids. It can also be advantageous, however, to perform the neutralization by means of inorganic bases (hydroxides, carbonates or bicarbonates) of sodium, potassium or lithium.

To produce the neutral salts, enough of the desired base can be added to the acid chelate salts in an aqueous solution or suspension that the point of neutrality is reached. The resulting solution can then be concentrated to dryness in vacuo. It is often advantageous to precipitate the neutral salts by adding a solvent miscible with water, for example, lower alcohols (methyl, ethyl, isopropyl alcohols, etc.), lower ketones (acetone, etc.), polar ethers (tetrahydrofuran, 1,2-dimethoxyethane, etc.) and thus obtain crystals that isolate easily and purify well. It has been found particularly advantageous to add the desired bases to the reaction mixture even during chelating and thus eliminate a process stage. Other conventional purification procedures such as column chromatography can be used.

Since the chelate salts of Formulas II, III and IV contain a plurality of acid groups, it is possible to produce neutral mixed salts which contain both inorganic and organic physiologically biocompatible cations as counterions. This can be done, for example, by reacting the complexing acids in an aqueous suspension or solution with the oxide or salt of the element supplying the central ion or less than the full amount of an organic base necessary for neutralization, e.g., half, isolating the chelate salt that is formed, purifying it, if desired, and then adding it to the amount of inorganic base necessary for complete neutralization. The sequence of adding the bases can be reversed.

The carboxylic and phosphoric acid groups of the chelating agents can also be neutralized by esterification to prepare carboxylate and phosphate esters. Such esters can be prepared by conventional procedures known in the art, for example, from the corresponding alcohols. Suitable esters include, for example, esters of straight or branch-chained alkanol groups having from 1 to 18 carbons, mono and polyhydric alkyl amino alcohols having from 1 to 18 carbons and preferably from 1 to 6 carbons such as serinol or diethanolamine, and polyhydric alcohols having from 1 to 18 and preferably from 1 to 6 carbons such as ethylene glycol or glycerol.

The diagnostic media for administration is formed using physiologically acceptable media in a manner fully within the skill of the art. For example, the chelate salts, optionally with the addition of pharmaceutically acceptable excipients, are suspended or dissolved in an aqueous medium, and then the solution or suspension is sterilized. Suitable additives include, for example, physiologically biocompatible buffers (as, for example, tromethamine hydrochloride), slight additions of other chelating agents (as for example, diethylenetriaminepentacetic acid) or, optimally, calcium salts (for example, calcium chloride, calcium ascorbate, calcium gluconate or calcium lactate).

The usual mode for administering radioactive metal ion chelates as radioimaging agents is by intravenous administration. Intraveneous solutions must be sterile, free from physiologically unacceptable agents, and should be isotonic or iso-osmotic to minimize irritation or other adverse effects upon administration. Suitable vehicles are aqueous vehicles customarily used for administering parenteral solutions such as Sodium Chloride Injection, Ringer's Injection, Dextrose Injection, Dextrose and Sodium Chloride Injection, Lactated Ringer's Injection, and other solutions such as are described in REMINGTON'S PHARMACEUTICAL SCIENCES. 15th Ed., Easton: Mack Publishing Co. pp 1405–1412 and 1461–1487 (1975) and THE NATIONAL FORMULARY XIV. 14th Ed. Washington: American Pharmaceutical Association (1975), the contents of which are hereby incorporated by reference. The solutions can contain preservatives, antimicrobial agents, buffers and antioxidants conventionally used in parenteral solutions, selecting excipients and other additives which are compatible with the chelates and which will not interfere with the manufacture, storage or use of the products.

The technetium-99m diagnostic media according to this invention can contain from 0.01 to 10 mCi/ml and preferably from 2 to 5 mCi/ml of the chelate salt.

The chelates of this invention are administered to patients for imaging in amounts which are sufficient to yield the desired image. Generally, dosages of from 0.001 to 1 mCi of imaging agent per kilogram of patient body weight are effective to obtain an image of most organs. The preferred dosages for most radiochemical imaging applications are from 0.002 to 0.1 mCi of imaging agent per kilogram of patient body weight.

Methods for applying the radiochemical agents for imaging, and the equipment and methods for imaging are described by Alazraki, N., et al, FUNDAMENTALS OF NUCLEAR MEDICINE. New York: The Society of Nuclear Medicine, Inc. (1984); THE CHEMISTRY OF RADIOPHARMACEUTICALS. Heindel, N. et al, Editors, Chicago: Masson Publishing (1978); and RADIOPHARMACEUTICALS: PROGRESS AND CLINICAL PERSPECTIVES. Fritzberg, A. Editor, Boca Raton: CRC Press (1986), and the publications cited therein, the entire contents of each of these publications and the reference citations included therein being hereby incorporated by reference in their entireties. These chelates can be formulated and administered in the same manner as the radiochemical chelates described in U.S. Pat. Nos. 4,313,928, 4,440,739 and 4,489,053, for example.

These reagents can be administered orally, intravenously, by enema, or lavage.

CHELATE FORMING COMPOUNDS

The compounds of Formula I can be formed by reacting the corresponding pyridoxal 5-phosphate,(3-hydroxy-2-methyl-5-phosphonomethyl-4-pyridinecarboxaldehyde) represented by Formula V with a diamine represented by Formula VI.

In the compounds of Formula V, $R_3$ and $R_4$ are as defined with respect to Formula I. Pyridoxyl 5-phosphate, pyridoxal, and the other compounds of Formula V, and the alkylenediamine, cycloalkylenediamine and arylene reactants of Formula VI are well known compounds readily available from commercial sources, and they can be readily synthesized by well known procedures fully within the skill of the art.

The reaction of the amino groups of the compounds of Formula VI with the aldehyde group of the compounds of Formula V can be carried out in an alcohol such as methanol at a temperature within the range of from 0° to 60° C. The diimines formed are represented by Formula VII.

In the compounds of Formula V, $R_3$ and $R_4$ are the same as described with respect to the compounds of Formula I. For the manufacture of compounds wherein $R_4$ is a phosphonomethyl group, i.e., the 5-(N-(3-hydroxy-2-methyl-5-phosponomethyl-4-pyridyl)methylideneaminoalkyleneiminomethyl)-2-hydroxy-3-methyl-5-pyridylmethylphosphoric acids, 5-(N-(3-hydroxy-2-methyl-5-phosponomethyl-4-pyridyl)methylideneamino-1,2-cycloalkyleneiminomethyl)-2-hydroxy-3-methyl-5-pyridylmethyl phosphoric acids, and 5-(N-(3-hydroxy-2-methyl-5-phosponomethyl-4-pyridyl)-methylideneamino- 1,2-aryleneiminomethyl)-2-hydroxy-3-methyl-5-pyridylmethyl phosphoric acids of Formula VI, a diamine of Formula VI is reacted with two molar equivalents of an aldehyde of Formula V having the 5-phosphonomethyl group such as pyridoxyl 5-phosphate. For preparation of compounds of Formula VII wherein $R_4$ is other than a phosphonomethyl group, the diamine of Formula VI is first reacted with only one molar equivalent of an aldehyde of Formula V having the 5-phosphonomethyl group, and the mono-phosphonomethyl reaction product is reacted with one molar equivalent of a compound of Formula V having the desired $R_4$ group, such as a 5-hydroxymethyl group, i.e, pyridoxal. The reverse order of reaction can also be used. The reaction products of Formula VII are insoluble in the alcohol and can be isolated by filtration.

The compounds of Formula VII are then hydrogenated by conventional procedures using a palladium or platinum catalyst to yield the diamines of Formula VIII.

In the compounds of Formula VIII, $R_3$ $R_4$ are the same as described with respect to the compounds of Formula IV. The 5-(N-(3-hydroxy-2-methyl-5-phosponomethyl-4-pyridyl)-methylaminoalkyleneaminomethyl)-2-hydroxy- 3--methyl-5-pyridylmethylphosphoric acids, 5-(N-(3-hydroxy-2-methyl-5-phosponomethyl-4-pyridyl)methylamino-1,2-cycloalkyleneaminomethyl)-2-hydroxy3-methyl-5-pyridylmethyl phosphoric acids, 5-(N-(3-hydroxy-2-methyl-5-phosponomethyl-4-pyridyl)methylamino-1,2-cycloaryleneaminomethyl)-2-hydroxy-3-methyl-5-pyridylmethyl phosphoric acids, and the monophosphonomethyl compounds of Formula VIII can be left in solution or isolated as crystalline solids.

The compounds of Formula I are prepared by reacting the diamines of Formula VIII with a haloacetic acid such as bromoacetic acid, the molar ratio of the bromoacetic acid to diamine determining whether one or both of the amines are conjugated with the acetic acid groups. The N,N'-bis(3-hydroxy-2-methyl-5-phosphonomethyl-4-pyridylmethyl)alkylenediamine-N,N'-diacetic acids, N,N'-bis(3-hydroxy-2-methyl-5-phosphonomethyl-4-pyridylmethyl)-1,2-cycloalkylenediamine-N,N'-diacetic acids, N,N'-bis(3-hydroxy-2-methyl-5-phosphonomethyl-4-pyridylmethyl)-1,2-arylenediamine-N,N'-diacetic acids, N,N'-bis(3-hydroxy-2-methyl-5-phosphonomethyl-4-pyridylmethyl)alkylenediamine-N-acetic acids, N,N'-bis(3-hydroxy-2-methyl-5-phosphonomethyl-4-pyridylmethyl)-1,2-cycloalkylenediamine-N-acetic acids, and N,N'-bis(3-hydroxy-2-methyl-5-phosphonomethyl-4-pyridylmethyl)-1,2-arylenediamine-N-acetic acids of Formula I are then isolated and purified by conventional procedures such as recrystallization or anion exchange chromatography.

The carboxylic acid esters and amides can be formed by conventional procedures reacting the carboxylic acids with alkanols having from 1 to 18 carbons, hydroxy-substituted alkanols having from 1 to 18 carbons, ammonia, and alkylamines having from 1 to 18 carbons.

This invention is further illustrated by the following specific but non-limiting examples. Temperatures are given in degrees centigrade and concentrations as weight percents unless otherwise specified. Procedures which are constructively reduced to practice herein are described in the present tense, and procedures which have been carried out in the laboratory are set forth in the past tense.

EXAMPLE 1

N,N'-bis(pyridoxal-5-phosphate)ethylenediimine

A 265.2 gm (1 mole) quantity of pyridoxal-5-phosphate (Chemical Dynamics Corp., South Plainfield, N.J.) was slurried in one liter of methanol, and 400 ml of 5 M NaOH was added. When the solution was homogeneous, 34.2 ml of 1,2-diaminoethane (Aldrich Chem. Co.) was added rapidly with vigorous stirring. The imine product sodium N,N'-bis(pyridoxal-5-phosphate)ethylenediimine or sodium 5-(N-(3-hydroxy-2-methyl-5-phosponomethyl-4-pyridyl)methylideneaminoethyleneiminomethyl)-2-hydroxy-3-methyl-5-pyridylmethylphosphate was stirred for 1 hr, 400 ml of diethyl ether was added, and the slurry was filtered. The filtrate was washed with 600 ml of ethanol and dried at 60° C. in vacuo. A 290 gm quantity of the bis-imine with a melting point of 215°–220° C. (decomposition) was isolated (90% yield, based on the tetrasodium salt).

IR (KBr) pellet: 1630 cm$^{-1}$ (C=N), $^1$H NMR (D$_2$O, 400 MHz) delta 8.88 (s, —N=CH), 7.54 (s, pyr-H), 4.70 (d, CH$_2$OP, J$_{HP}$=6.3 Hz), 4.06 (s, NCH$_2$CH$_2$N), 2.21 (s, pyr-CH$_3$).

EXAMPLE 2

N,N,-bis(pyridoxal-5-phosphate)alkyldiimines Repeating the procedure of Example 1 but replacing the 1,2-diaminoethane with 1,3-diamino-n-propane, 1,2-diamino-n-propane, 1,2-diaminoisopropane, 1,2-diamino-n-butane, 1,4-diamino-n-butane, 1,3-diamino-n-butane, 1,2-diamino-3-methylpropane yields the corresponding N,N'-bis(pyridoxal-5-phosphate)-1,3-(n-propylene)diimine, N,N'-bis(pyridoxal-5-phosphate)-1,2-(n-propylene)diimine, N,N'-bis(pyridoxal-5-phosphate)-1,2-isopropylenediimine, N,N'-bis(pyridoxal-5-phosphate)-1,2-(n-butylene)diimine, N,N'-bis(pyridoxal-5-phosphate)-1,4-(n-butylene)diimine, N,N'-bis(pyridoxal-5-phosphate)-1,3-(n-butylene)diimine, and N,N'-bis(pyridoxal-5-phosphate)-1,2-(3-methyl)propylenediimine.

EXAMPLE 3

N,N'-bis(pyridoxal-5-phosphate)ethylenediamine

The diimine from Example 1 was charged to a 5 liter 3-neck flask fitted with mechanical stirrer, fritted tube bubbler, and a 3-way stopcock. Then 1.5 liters of deronized water was added, followed by 1.5 liters of methanol. The yellow solution formed was stirred while sparging with nitrogen. Then 13 gm of 5% Pt on carbon (Aldrich Chem. Co.) was added, and the apparatus was purged with hydrogen. The reaction was allowed to proceed for 5 hr with continuous addition of hydrogen. HPLC analysis showed complete reduction to the amine. The reaction mixture was sparged with nitrogen for 15 min and then filtered through Celite. The filtrate was concentrated in vacuo at 60° C to about 500 ml. The solution, containing N,N'-bis(pyridoxal-5-phosphate)ethylenediamine or 5-(N-(3-hydroxy-2-methyl-5-phosponomethyl-4-pyridyl)methylaminoethyleneaminomethyl)-2-hydroxy-3-methyl-5-pyridylmethylphosphoric acid salt was used directly for the next step. If desired the diamine can be isolated as off-white crystals by the addition of 200 ml of 97% formic acid and allowing the product to crystallize at room temperature overnight. The diamine is isolated by filtration and washed with 2×150 ml of cold deionized water.

$^1$H NMR (D$_2$O, 400 MHz) delta 7.47 (s, pyr-H), 4.58 (d, CH$_2$OP, J$_{HP}$=6.3 Hz), 3.94 (s, NCH$_2$CH$_2$N), 2.88 (s, N-CH$_2$-pyr), 2.16 (s, pyr-CH$_3$)

EXAMPLE 4

N,N'-bis(pyridoxal-5-phosphate)alkyldiamines

Repeating the procedure of Example 3 but substituting the diimine products of Example 2 for the diimine product of Example 1 yields N,N'-bis(pyridoxal-5-phosphate)-1,3-(n-propylene)diamine, N,N'-bis(pyridoxal-5-phosphate)-1,2-(n-propylene)diamine, N,N'-bis(pyridoxal-5-phosphate)-1,2-isopropylenediamine, N,N'-bis(pyridoxal-5-phosphate)-1,2-(n-butylene)diamine, N,N'-bis(pyridoxal-5-phosphate)-1,4-(n-butylene)diamine, N,N'-bis(pyridoxal-5-phosphate)-1,3-(n-butylene)diamine, and N,N'-bis(pyridoxal-5-phosphate)-1,2-(3-methyl)propylenediamine.

EXAMPLE 5

DPDP Synthesis

The diamine from Example 3 was charged to a two liter 4-neck flask equipped with two addition funnels, pH electrode, thermometer and stir bar. A 100 gm (2.5 mole) quantity of NaOH was dissolved in 200 ml of deionized water, and 130 gm (0.9 mole) of bromoacetic acid (Sigma Chem. Co.) was dissolved in 180 ml of deionized water. Each solution was charged to an addition funnel. Enough NaOH solution was added to the diamine solution to bring the pH to 11. The temperature of the reaction was raised to 42° C., and bromoacetic acid and NaOH solution were added concurrently to maintain the pH at 11. The addition was stopped at 45 min, and the progress of the reaction was checked by HPLC. The addition of bromoacetic acid and NaOH was resumed, and the reaction checked at 60 and 75 min. All the bromoacetic acid had been added, and the reaction was complete by HPLC analysis. Approximately 30 ml of the 50% NaOH solution remained in the addition funnel. A 675 gm quantity of cation exchange resin (AMBERLITE IRC-50) was added, and the mixture was placed in a refrigerator for 14 hr. The pH had dropped to 6.5. The resin was removed by filtration, and the filtrate treated with 260 gm of cation exchange resin (DOWEX 50W-X8). The pH dropped to about 4. The resin was removed by filtration, and the solution was concentrated in vacuo at 60° C. to a viscous oil. The oil was dried in vacuo for 48 hr at 25° C. to yield a resinous solid containing N,N,-bis-(pyridoxal-5-phosphate)ethylene-diamine-N,N'-diacetic acid or N,N,-bis(3-hydroxy-2-methyl-5-phosphonomethyl-4-pyridylmethyl)ethylene-diamine-N,N'-diacetic acid (DPDP).

EXAMPLE 6

DPDP Purification

The resinous solid obtained in Example 5 was dissolved in 600 ml of 88% formic acid, 1.5 liters of methanol followed by 2.2 liters of ethanol was added, and the mixture was cooled to 0° C. for 2 hr. The solvent mixture was decanted from the resulting gum and discarded. The gum was dissolved in about 800 ml of deionized water which wa then concentrated in vacuo to about 600–650 ml. Seed crystals were added, and the solution was allowed to stand at rm temp overnight. The product was isolated by filtration, washed with about 400 ml of cold deionized water, 250 ml of ethanol, and then dried in vacuo to yield 65 gm of DPDP in 85–90% purity by HPLC. The filtrate and washings were retained, concentrated in vacuo to about 350 ml, and the solution refrigerated until column chromatographic purification of the second crop.

The 65 gms of product was then dissolved in 75 ml of 88% formic acid containing 5 ml of deionized water with gentle heating to about 60° C. Cold deionized water was added to a total volume of one liter, and the solution was allowed to stand at 25° C. for 16 hr to crystallize. The product was isolated by filtration, washed with 200 ml cold deionized water, and dried in vacuo at 60° C. to yield 55 gms of DPDP in 93–95% purity by HPLC. A second recrystallization, using the same procedure yields 50 gm of DPDP in 96–98% purity by HPLC, mp 174°–80° C. with decomposition.

Analysis: (Calculated for C$_{22}$H$_{32}$N$_4$O$_{14}$P$_2$)C, 41.38; H, 5.05; N, 8.77. (Found) C, 40.70; H, 5.14; N, 8.61.

$^1$H NMR (D$_2$O, 400 MHz) delta 7.93 (s, pyr-H), 4.81 (d, CH$_2$OP, J$_{HP}$=6.3 Hz), 4.07 (s, NCH$_2$CH$_2$N), 3.35 (s, CH$_2$COOH), 2.83 (s, N-CH$_2$-pyr), 2.38 (s, pyr-CH$_3$).

$^{31}$P NMR (D$_2$O, −161 MHz) delta −1.61 (s, CH$_2$OP, H$_3$PO$_4$ reference).

EXAMPLE 7

Sodium-Calcium Salt of Tc(DPDP)

A 64 gm (0.1 mmole) portion of DPDP from Example 6 is dissolved in 1.0 ml of rigorously degassed water for injection containing 8 mg (0.2 mmole) of NaOH, 2.2 mg (0.02 mmole) $CaC_2$, 59 gm sodium citrate (0.02 mmole) and 28 mg (0.15 mmole) stannous chloride. In a vial flushed with nitrogen gas, the above solution is admixed with a physiological saline solution containing $^{99m}Tc$ (10 mCi) in the form of sodium pertechnetate obtained by saline elution from a standard, commercially available (New England Nuclear) $^{99}Mo$-$^{99m}Tc$ alumina generator described by Heindel, N. et al, (supra, p 156). The solution is stirred well and heated to 100° C. for 5 min and then cooled at rm temp to yield a colorless, transparent solution. The solution is sterilized by being filtered through a 0.2 micron filter to yield the sodium-calcium salt of a technetium-99m chelate complex of N,N'-bis-(pyridoxal-5-phosphate)ethylenediamine-N,N'-diacetic acid or N,N'-bis(3-hydroxy-2-methyl-5-phosphonomethyl-4-pyridylmethyl)ethylenediamine-N,N'-diacetic acid.

EXAMPLE 8

Potentiometric Titrations

The compound DPDP was studied potentiometrically from pH 11.2 to 2.0. Data sets were collected on a custom-built automatic potentiometric titration apparatus composed of a METROHM 655 DOSIMAT automatic buret, a FISHER ACCUMET pH meter with a CORNING calomel combination electrode, a custom-blown water jacketed titration cell, a BRINKMAN LAUDA K-2/R constant temperature bath and a COMMODORE 64 computer. The BASIC computer program TITRATOR (Harris, W. et al, *J. Am. Chem. Soc.* 101:6534 (1979)) runs the apparatus. Data analysis was performed on an IBM-AT computer using the least squares program, BETA (Harris, W. et al, supra), and the data analysis program, HANDNBAR (Harris, W. et al, supra). The titrants were standardized by phenophthalein titration a follows: KOH was calibrated against potassium hydrogen phthalate (a primary standard), and HCl solutions were calibrated against the KOH standard. All solutions were made from distilled, deionized water that was further purified on a MILLI-Q cartridge system, degassed, and then kept under an atmosphere of argon which had been scrubbed for $CO_2$ and $O_2$. Additions of EDTA solutions were performed using calibrated GILMOT pipets. The electrode was calibrated in concentration units with degassed solutions of p[H+]=2.291 and 078 at 0.1 M ionic strength.

The ligand proton titration was performed by adding 28.7 mg (0.045 mmoles) to 54.6 ml of a high pH aqueous solution. It was then titrated to low pH with 0.1009 N HCl.

Figure 1:
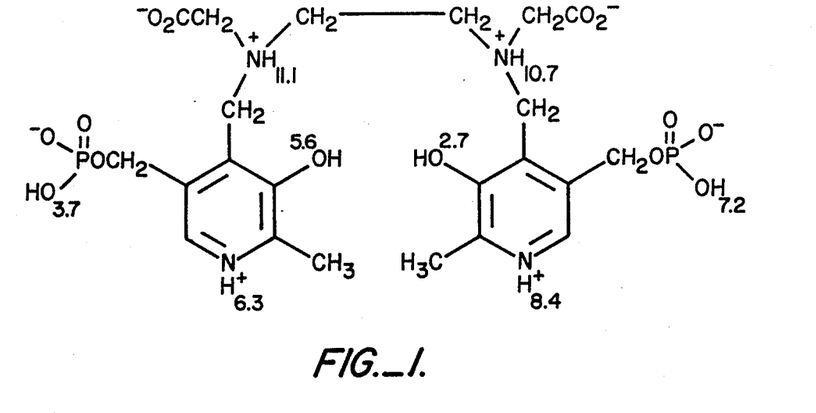
FIG. 1 shows a structural formula of a species of N,N'-bis(pyridoxal-5-phosphate)ethylenediamine-N,N'-diacetic acid, showing the dissociation constants, pK's, which are assigned to the protonation sites as described in Example 8.

The data obtained was analyzed using a model that consisted of eight one-proton steps. The first two protonation equilibria were outside of the range of the titration window afforded by the concentration of titrant and were therefore estimated based on work by Martell and Taliaferro, C. et al, *Inorg. Chem.* 24:2408–2413 (1985). Refinement of the remaining equilibria yielded constants with calculated e.s.d.'s (log K) of less than 0.02. Assignment of the protonation sites (pK's) was based on work by Martell and co-workers (Taliaferro, et al, supra), and is shown in FIG. 1.

At a pH of 3 and above, the ligand is anionic and possesses deprotonated metal binding sites, both important criteria for a metal chelating agent.

EXAMPLE 9

N,N'-bis-(pyridoxal-5-phosphate)-alkylenediamine-N,N'-diacetic acids

Repeating the procedure of Examples 5 and 6 but replacing the diamine of Example 3 with the products of Example 4 yields N,N'-bis(pyridoxal-5-phosphate)-1,3-(n-propylene)-N,N'-diacetic acid, N,N'-bis(pyridoxal-5-phosphate)-1,2-(n-propylene)-N,N'-diacetic acid, N,N'-bis(pyridoxal-5-phosphate)-1,2-isopropylene-N,N'-diacetic acid, N,N'-bis(pyridoxal-5-phosphate)-1,2-(n-butylene)-N,N'-diacetic acid, N,N'-bis(pyridoxal-5-phosphate)-1,4-(n-butylene)-N,N'-diacetic acid, N,N'-bis(pyridoxal-5-phosphate)-1,3-(n-butylene)-N,N'-diacetic acid, and N,N'-bis(pyridoxal-5-phosphate)-1,2-(3-methylene)propyl-N,N'-diacetic acid.

EXAMPLE 10

DPDP Chelates

Repeating the procedure of Example 7 but replacing the technetium-99m with equimolar amounts of the soluble chlorides, sulfates, nitrates or carbonates of $^{99}Tc$ and $^{95}Tc$, and the reduced technetium-99m with the soluble chlorides, sulfates, nitrates or carbonates of $^{51}Cr(III)$, $^{57}Co(II)$, $^{67}Ga(III)$, $^{68}Ga(III)$, $^{111}In(III)$, $^{113m}In(III)$, $^{197}Hg(II)$, $^{75}Se(IV)$, $^{201}Tl(III)$, $^{203}Pb(II)$, $^{85}Sr(II)$, $^{87m}Sr(II)$, $^{135m}Sm(III)$, $^{153}Sm(III)$, $^{171}Er(III)$, $^{169}Yb(III)$, $^{62}Zn(II)$, and $^{186}Re(III)$ yields the corresponding sodium-calcium salts of the respective radioactive metal ion chelates of N,N'-bis-(pyridoxal-5-phosphate)ethylenediamine-N,N'-diacetic acid.

EXAMPLE 11

Other Chelates

Repeating the procedure of Example 7 but replacing N,N'-bis-(pyridoxal-5-phosphate)ethylenediamine-N,N'-diacetic acid with equimolar amounts of the chelate forming compounds produced in accordance with Example 9, and using equimolar amounts reduced $^{99m}Tc$ and $^{95}Tc$ and with equimolar amounts of the soluble chlorides, carbonates or nitrates of $^{99}Tc$, $^{51}Cr(III)$, $^{57}Co(II)$, $^{67}Ga(III)$, $^{68}Ga(III)$, $^{111}In(III)$, $^{113m}In(III)$, $^{197}Hg(II)$, $^{75}Se(IV)$, $^{201}Tl(III)$, $^{203}Pb(II)$, $^{85}Sr(II)$, $^{87m}Sr(II)$, $^{135m}Sm(III)$, $^{153}Sm(III)$, $^{171}Er(III)$, $^{169}Yb(III)$, $^{62}Zn(II)$ and $^{186}Re(III)$ yields the sodium-calcium salts of the respective radioactive metal ion chelates of N,N'-bis(pyridoxal-5-phosphate)-1,3-(n-propylene)-N,N'-diacetic acid, N,N'-bis(pyridoxal-5-phosphate)-1,2-(n-propylene)-N,N'-diacetic acid, N,N'-bis(pyridoxal-5-phosphate)-1,2-isopropylene-N,N'-diacetic acid, N,N'-bis(pyridoxal-5-phosphate)-1,2-(n-butylene)-N,N'-diacetic acid, N,N'-bis(pyridoxal-5-phosphate)-1,4-(n-butylene)-N,N'-diacetic acid, N,N'-bis(pyridoxal-5-phosphate)-1,3-(n-butylene)-N,N'-diacetic acid, and N,N'-bis(pyridoxal-5-phosphate)-1,2-(3-methylene)propyl-N,N'-diacetic acid.

EXAMPLE 12

N,N'-bis(pyridoxal-5-phosphate)-trans-1,2-cyclohexylenediimine

A 26.5 gm quantity (0.1 mole) of pyridoxal-5-phosphate was dissolved in 300 ml of methanol, and 38 ml of 5 N NaOH was added. Then 5.71 gm (0.05 mole) of trans-1,2-diaminocyclohexane was added with stirring, and the volume of the solution was reduced to 200 ml in vacuo. After cooling to 0° C., the yellow imine was isolated by filtration, washed with diethyl ether, and dried in vacuo to yield 17 gm of sodium N,N'-bis(pyridoxal-5-phosphate)-trans-1,2-cyclohexylenediimine or sodium 5-(N-(3-hydroxy-2-methyl-5-phosphonomethyl-4-pyridyl)methylideneamino-trans-1,2-cyclohexyleneiminomethyl)-2-hydroxy-3-methyl-5-pyridylmethylphosphate (49% yield, melting point 200°–205° C. with decomposition).

EXAMPLE 13

Other N,N'-bis(pyridoxal-5-phosphate)-1,2-cyclo(alkylene or arylene)diimines

Repeating the procedure of Example 12 but replacing the trans-1,2-diaminocyclohexane with trans-1,2-diaminocyclopentane, trans-1,2-diaminocycloheptane, trans-1,2-diaminocyclooctane, cis-1,2-diaminocyclohexane, trans-1,3-diaminocyclohexane, trans-1,4-diaminocyclohexane, o-aminoaniline and cis-1,4-diaminocyclohexane yields the corresponding N,N'-bis(pyridoxal-5-phosphate)-trans-1,2-cyclopentylenediimine, N,N'-bis(pyridoxal-5-phosphate)-trans-1,2-cycloheptylenediimine, N,N'-bis(pyridoxal-5-phosphate)-trans-1,2-cyclooctylenediimine, N,N'-bis(pyridoxal-5-phosphate)-1,2-phenylenediimine, and N,N'-bis(pyridoxal-5-phosphate)-cis-1,2-cyclohexylenediimine.

EXAMPLE 14

N,N'-bis(pyroxidal-5-phosphate)-trans-1,2-cyclohexylenediamine

A 14 gm (0.02 mole) portion of the diimine product of Example 12 was dissolved in 200 ml of 1:1 water:methanol. The resulting solution was sparged with argon, and 1.0 gm of 5% platinum on carbon was added. The system was flushed with hydrogen. The hydrogen pressure was increased to 50 psig for 16 hr at 25° C. The reaction product was filtered through CELITE, and the resulting solution of N,N'-bis(pyridoxal-5-phosphate)-trans-1,2-cyclohexyldiamine or sodium 5-(N-(3-hydroxy-2-methyl-5-phosphonomethyl-4-pyridyl)-methylideneamino-trans-1,2-cyclohexyliminomethyl)-2-hydroxy-3-methyl-5-pyridylmethylphosphate was concentrated in vacuo to about 20 ml and cooled to 0° C. to induce crystallization. The product was isolated by filtration, washed with cold H$_2$O and dried in vacuo.
$^1$H NMR (D$_2$O, 400 MHz) delta 7.45 (s, pyr-H), 4.53 (d, CH$_2$OP, JH$_P$=4.9 Hz), 3.83 (dd, N-CH$_2$-pyr), 2.72 (br s, cyclo-(CH$_2$)$_4$(CH)$_2$(NH)$_2$), 1.88 (s, pyr-CH$_3$), 1.83–1.08 (3 br s, cyclo-(CH$_2$)$_4$(CH)$_2$(NH)$_2$).

EXAMPLE 15

N,N'-bis(pyridoxal-5-phosphate)-1,2-cyclo(alkylene or arylene)diamines

Repeating the procedure of Example 14 but replacing the diimine product of Example 12 with the diimine products prepared in accordance with the procedure of Example 13 yields the corresponding diamines:

N,N'-bis(pyridoxal-5-phosphate)-trans-1,2-cyclopentylenediamine,

N,N'-bis(pyridoxal-5-phosphate)-trans-1,2-cycloheptylenediamine,

N,N'-bis(pyridoxal-5-phosphate)-trans-1,2-cyclooctylenediamine,

N,N'-bis(pyridoxal-5-phosphate)-1,2-phenylenediamine, and

N,N'-bis(pyridoxal-5-phosphate)-cis-1,2-cyclohexylenediamine.

EXAMPLE 6

N,N'-bis-(pyridoxal-5-phosphate)-trans-1,2-cyclohexylenediamine-N,N'-diacetic acid The diamine from Example 17 was charged to a one liter 3-neck flask, and the pH was adjusted to 11 with 5 N NaOH. Then 5.6 gm (0.04 mole) of bromoacetic acid was dissolved in 10 ml of water and added dropwise to the stirred diamine solution while maintaining the pH at 11. The reaction was warmed to 50° C. and stirred for 16 hr. 50 gm of weakly acidic cation exchange resin (AMBERLITE IRC-50) was added, and the pH dropped to 6.7. The resin was removed by filtration, and 15 gm of cation exchange resin (DOWEX 50W-X8) was added. The pH dropped to 3.8.

The solution was filtered, and all of the solvent was evaporated from the filtrate to yield a foamy solid. The solid was dissolved in 30 ml of 88% formic acid, and the product was precipitated by the addition of 150 ml of methanol followed by 150 ml of ethanol. The solvent mixture was decanted from the gummy solid and discarded. The solid was dissolved in a minimum amount of deionized water (about 100 ml), and the product was allowed to stand overnight at 25° C. The product was isolated by filtration, washed with 50 ml of cold water, 25 ml of ethanol and then dried in vacuo to yield the product. The compound was recrystallized by the same procedure to yield N,N'-bis-(pyridoxal-5-phosphate)-trans-1,2-cyclohexylenediamine-N,N'-diacetic acid or N,N'-bis(3-hydroxy-2-methyl-5-phosphonomethyl-4-pyridylmethyl)-trans-1,2-cyclohexylenediamine-N,N'-diacetic acid (DPCP) with a melting point (decomposition) of 221°–226° C.

$^1$H NMR (D$_2$O, 400 MHz) delta 7.53 (s, pyr-H), 4.58 (d, CH$_2$OP, J$_{HP}$=5.9 Hz), 3.89 (dd, N-CH$_2$-pyr), 3.31 (s, CH$_2$COOH), 2.78 (br s, cyclo-(CH$_2$)$_4$(CH)$_2$(NH)$_2$—), 1.93 (s, pyr-CH$_3$), 1.90–1.15 (3 br s, cyclo-(CH$_2$)$_4$(CH)$_2$(NH)$_2$—).

EXAMPLE 17

N,N'-bis-(pyridoxal-5-phosphate)-cyclo(alkylene and arylene)diamine-N,N'-diacetic acids Repeating the procedure of Example 16 but replacing the diamine of Example 14 with the diamines of Example 15 yields the corresponding:

N,N'-bis(pyridoxal-5-phosphate)-trans-1,2-cyclopentylene-diamine-N,N'-diacetic acid, N,N'-bis(pyridoxal-5-phosphate)-trans-1,2-cycloheptylene-diamine-N,N'-diacetic acid,
N,N'-bis(pyridoxal-5-phosphate)-trans-1,2-cyclooctylenedimine-N,N'-diacetic acid,
N,N'-bis(pyridoxal-5-phosphate)-1,2-phenylenediamine-N,N'-diacetic acid, and
N,N'-bis(pyridoxal-5-phosphate)-cis-1,2-cyclohexylenediamine-N,N'-diacetic acid.

EXAMPLE 18

Chelates

Repeating the procedure of Example 7 but replacing N,N'-bis-(pyridoxal-5-phosphate)ethylenediamine-N,N'-diacetic acid with equimolar amounts of the products of chelate forming compounds produced in accordance with Examples 16 and 17 and using equimolar amounts of reduced $^{99m}Tc$, $^{95}Tc$ and $^{99}Tc$ and with the soluble chlorides, carbonates or nitrates of $^{51}Cr(III)$, $^{57}Co(II)$, $^{67}Ga(III)$, $^{68}Ga(III)$, $^{111}In(III)$, $^{113m}In(III)$, $^{917}Hg(II)$, $^{75}Se(IV)$, $^{201}Tl(III)$, $^{203}Pb(II)$, $^{85}Sr(II)$, $^{87m}mSr(II)$, 135mSm(III), $^{153}Sm(III)$, $^{171}Er(III)$, $^{169}Yb(III)$, $^{62}Zn(II)$ and $^{186}Re(III)$ yields the sodium-calcium salts of the respective radioactive metal ion chelates of
N,N'-bis(pyridoxal-5-phosphate)-trans-1,2-cyclopentylenediamine-N,N'-diacetic acid,
N,N'-bis(pyridoxal-5-phosphate)-trans-1,2-cycloheptylenediamine-N,N'-diacetic acid,
N,N'-bis(pyridoxal-5-phosphate)-trans-1,2-cyclooctylenediamine-N,N'-diacetic acid,
N,N'-bis(pyridoxal-5-phosphate)-1,2-phenylenediamine-N,N'-diacetic acid, and
N,N'-bis(pyridoxal-5-phosphate)-cis-1,2-cyclohexylenediamine-N,N'-diacetic acid.

EXAMPLE 19

Pyridoxal-5-phosphate (N-methylethanolamine)monoester 2.04 gm (0.01 mole) of pyridoxal hydrochloride is dissolved in 50 ml of dry THF containing 0.05 gm (0.02 mole) of sodium hydride with stirring. When gas evolution had ceased (about 15min), 1.71 gm (0.01 mole) of benzyl bromide is added, and after stirring overnight, the solution is brought to dryness in vacuo. The sticky solid is suspended in 50 ml of dry methylene chloride and following addition of 3.0 gm (0.03 mole) of triethylamine, the slurry is cooled to 0° C. 1.38 gm (0.01 mole) of 2-chloro-3-methyl-l-oxa-3-aza-2-phosphacyclopentane (prepared by the method of Jones, et al, *J.Chem.Soc. Perkin trans I.* p 199 (1985)) is added with vigorous stirring. The suspension is stirred for 1 hr at rm temp, and then 100 ml of water is added. The methylene chloride layer is separated, dried over MgSO$_4$, and the solvent removed in vacuo. Addition of diethyl ether yields the intermediate product as a hydroscopic white solid (1.8 gm, 50% yield). The intermediate is oxidized with excess dinitrogen tetroxide in methylene chloride at −78° C., and then is treated with aqueous HCl in THF under reflux to give the (N-methylethanolamine)monoester of pyridoxal-5-phosphate in an overall yield of 40%.

EXAMPLE 20

N,N'-bis(pyridoxal-5-phosphate(N-methylethanolamine) monoester)ethylenediimine Repeating the procedure of Example 1 but replacing pyridoxal-5-phosphate with the product of Example 19 yields N,N'-bis(pyridoxal-5-phosphate(N-methylethanolamine) monoester)ethylenediimine or sodium 5-(N-(3-hydroxy-2-methyl-5-phosponomethyl-4-pyridyl)methylideneaminoethyleneiminomethyl)-2-hydroxy-3-methyl-5-pyridylmethylphosphoric acid, N-methylethanolamine ester.

EXAMPLE 21

Other Monoester Diimines

Repeating the procedure of Example 20 with 1,3-diamino-n-propane, 1,2-diamino-n-propane, 1,2-diaminoisopropane, 1,2-diamino-n-butane, 1,4-diamino-n-butane, 1,3-diamino-n-butane, and 1,2-diamino-3-methylpropane yields the corresponding
N,N'-bis(pyridoxal-5-phosphate(N-methylethanolamine)monoester)-1,3-(n-propylene)diimine,
N,N'-bis(pyridoxal-5-phosphate(N-methylethanolamine)monoester)-1,2-(n-propylene)diimine,
N,N'-bis(pyridoxal-5-phosphate(N-methylethanolamine)monoester)-1,2-isopropylenediimine,
N,N'-bis(pyridoxal-5-phosphate(N-methylethanolamine)monoester)-1,2-(n-butylene)diimine,
N,N'-bis(pyridoxal-5-phosphate(N-methylethanolamine)monoester)-1,4-(n-butylene)diimine,
N,N'-bis(pyridoxal-5-phosphate(N-methylethanolamine)monoester)-1,3-(n-butylene)diimine,
N,N'-bis(pyridoxal-5-phosphate(N-methylethanolamine)monoester)-1,2-(3-methyl)propylenediimine, Repeating the procedure of Example 20 with trans-1,2-diaminocyclohexane, trans-1,2-diaminocyclopentane, trans-1,2-diaminocycloheptane, trans-1,2-diaminocyclooctane, o-aminoaniline, and cis-1,2-diaminocyclohexane, yields the corresponding
N,N'-bis(pyridoxal-5-phosphate(N-methylethanolamine)monoester)-trans-1,2-cyclohexylenediimine,
N,N'-bis(pyridoxal-5-phosphate(N-methylethanolamine)monoester)-trans-1,2-cyclopentylenediimine,
N,N'-bis(pyridoxal-5-phosphate(N-methylethanolamine)monoester)-trans-1,2-cycloheptylenediimine,
N,N'-bis(pyridoxal-5-phosphate(N-methylethanolamine)monoester)-trans-1,2-cyclooctylenediimine,
N,N'-bis(pyridoxal-5-phosphate(N-methylethanolamine)monoester)-1,2-phenylenediimine, and
N,N'-bis(pyridoxal-5-phosphate(N-methylethanolamine)monoester)-cis-1,2-cyclohexylenediimine.

EXAMPLE 22

N,N'-bis(pyridoxal-5-phosphate(N-methylethanolamine)monoester)ethylenediamine Repeating the procedure of Example 3 but substituting the diimine product of Example 20 for the diimine product of Example 1 yields N,N'-bis(pyridoxal-5-phosphate(N-methyl-ethanolamine)monoester)ethylenediamine or 5-(N-(3-hydroxy-2-methyl-5-phosponomethyl-4-pyridyl)methylaminoethyleneaminomethyl)-2-hydroxy-3-methyl-5-pyridylmethylphosphoric acid, N-methyl-ethanolamine ester.

EXAMPLE 23

Other Monoester Diamines

Repeating the procedure of Example 22 but substituting the diamine products of Example 21 for the diamine product of Example 20 yields
N,N'-bis(pyridoxal-5-phosphate(N-methylethanolamine) monoester)-1,3-(n-propylene)diamine,
N,N'-bis(pyridoxal-5-phosphate(N-methylethanolamine) monoester)-1,2-(n-propylene)diamine,
N,N'-bis(pyridoxal-5-phosphate(N-methylethanolamine) monoester)-1,2-isopropylenediamine,
N,N'-bis(pyridoxal-5-phosphate(N-methylethanolamine)monoester)-1,2-(n-butylene)diamine,
N,N'-bis(pyridoxal-5-phosphate(N-methylethanolamine)monoester)-1,4-(n-butylene)diamine,
N,N'-bis(pyridoxal-5-phosphate(N-methylethanolamine)monoester)-1,3-(n-butylene)diamine,
N,N'-bis(pyridoxal-5-phosphate(N-methylethanolamine)monoester)-1,2-(3-methyl)propylenediamine,
N,N'-bis(pyridoxal-5-phosphate(N-methylethanolamine)monoester)-trans-1,2-cyclohexylenediamine,
N,N'-bis(pyridoxal-5-phosphate(N-methylethanolamine)monoester)-trans-1,2-cyclopentylenediamine,
N,N'-bis(pyridoxal-5-phosphate(N-methylethanolamine)monoester)-trans-1,2-cycloheptylenediamine,
N,N'-bis(pyridoxal-5-phosphate(N-methylethanolamine)monoester)-trans-1,2-cyclooctylenediamine,
N,N'-bis(pyridoxal-5-phosphate(N-methylethanolamine)monoester)-1,2-phenylenediamine, and
N,N'-bis(pyridoxal-5-phosphate(N-methylethanolamine)monoester)-cis-1,2-cyclohexylenediamine.

EXAMPLE 24

DPDP-phosphate monoester

Repeating the procedure of Examples 5 and 6 but replacing the diamine of Example 3 with the product of Example 22 yields N,N'-bis(pyridoxal-5-phosphate-(N-methyl-ethanolamine)monoester)ethylenediamine-N,N'-diacetic acid, sodium salt or N-methylethanolamine phosphate ester of 5-(N-(3-hydroxy-2-methyl-5-phosponomethyl-4-pyridyl)methylaminoethyleneaminomethyl)-2-hydroxy-3-methyl-5-pyridylmethylphosphoric acid, sodium salt.

EXAMPLE 25

Other Diamine-N,N'-diacetic Acid Phosphate Monoesters

Repeating the procedure of Example 24 but replacing the products of Example 23 for the product of Example 22 yields
N,N'-bis(pyridoxal-5-phosphate(N-methylethanolamine)monoester)-1,3-(n-propylene)diamine-N,N'-diacetic acid salt,
N,N'-bis(pyridoxal-5-phosphate(N-methylethanolamine)monoester)-1,2-(n-propylene)diamine-N,N'-diacetic acid salt,
N,N'-bis(pyridoxal-5-phosphate(N-methylethanolamine)monoester)-1,2-isopropylenediamine-N,N'-diacetic acid salt,
N,N'-bis(pyridoxal-5-phosphate(N-methylethanolamine)monoester)-1,2-(n-butylene)diamine-N,N'-diacetic acid salt,
N,N'-bis(pyridoxal-5-phosphate(N-methylethanolamine)monoester)-1,4-(n-butylene)diamine-N,N'-diacetic acid salt,
N,N'-bis(pyridoxal-5-phosphate(N-methylethanolamine)monoester)-1,3-(n-butylene)diamine-N,N'-diacetic acid salt,
N,N'-bis(pyridoxal-5-phosphate(N-methylethanolamine)monoester)-1,2-(3-methyl)propylenediamine-N,N'-diacetic acid salt,
N,N'-bis(pyridoxal-5-phosphate(N-methylethanolamine)monoester)-trans-1,2-cyclohexylenediamine-N,N'-diacetic acid salt,
N,N'-bis(pyridoxal-5-phosphate(N-methylethanolamine)monoester)-trans-1,2-cyclopentylenediamine-N,N'-diacetic acid salt,
N,N'-bis(pyridoxal-5-phosphate(N-methylethanolamine)monoester)-trans-1,2-cycloheptylenediamine-N,N'-diacetic acid salt,
N,N'-bis(pyridoxal-5-phosphate(N-methylethanolamine)monoester)-trans-1,2-cyclooctylenediamine-N,N'-diacetic acid salt,
N,N'-bis(pyridoxal-5-phosphate(N-methylethanolamine)monoester)-1,2-phenylenediamine-N,N'-diacetic acid salt, and
N,N'-bis(pyridoxal-5-phosphate(N-methylethanolamine)monoester)-cis-1,2-cyclohexylenediamine-N,N'-diacetic acid salt.

EXAMPLE 26

Chelates

Repeating the procedure of Example 7 but replacing N,N'-bis-(pyridoxal-5-phosphate)ethylenediamine-N,N'-diacetic acid with an equimolar amount of the chelate forming compound produced in accordance with Example 24, yields the sodium-calcium technetium-99m chelate of N,N'-bis(pyridoxal-5-phosphate-(N-methyl-ethanolamine)monoester)ethylenediamine-N,N'-diacetic acid.

Repeating this procedure, replacing reduced technician-99m with equimolar amounts of reduced $^{95}$Tc or $^{99}$Tc and with equimolar amounts of the soluble chlorides, carbonates or nitrates of $^{51}$Cr(III), $^{57}$Co(II), $^{67}$Ga(III), $^{68}$Ga(III), $^{111}$In(III), $^{113m}$In(III), $^{197}$Hg(II), $^{75}$Se(IV), $^{201}$Tl(III), $^{203}$Pb(II), $^{85}$Sr(II), $^{87m}$Sr(II), $^{135m}$Sm(III), $^{153}$Sm(III), $^{171}$Er(III), $^{169}$Yb(III), $^{62}$Zn(II) and $^{186}$Re (III) yields the sodium-calcium salts of the respective radioactive metal ion chelates of N,N'-bis(pyridoxal-5-phosphate-(N-methyl-ethanolamine)monoester)ethylenediamine-N,N'-diacetic acid.

EXAMPLE 27

Other Chelates

Repeating the procedures of Example 26 but replacing the products of Example 25 for the product of Example 24 yields the $^{99m}$Tc, $^{95}$Tc, $^{99}$Tc, $^{51}$Cr(III), $^{57}$Co(II), $^{67}$Ga(III), $^{68}$Ga(III), $^{111}$In(III), $^{113m}$In(III), $^{197}$Hg(II), $^{75}$Se(IV), $^{201}$Tl(III), $^{203}$Pb(II), $^{85}$Sr(II), $^{87m}$Sr(II), $^{135m}$Sm(III), $^{153}$Sm(III), $^{171}$Er(III), $^{169}$Yb(III), $^{62}$Zn(II) and $^{186}$Re (III) radioactive metal ion chelates of the sodium-calcium salts of the diacetic acid chelating agents of Example 25.

EXAMPLE 28

DPDP-(mono)acetic Acid Analog Synthesis 10 gms (0.017 mole) of the diamine from Example 3 was dissolved in 25 ml of 1:1 water/methanol and charged to a 250 ml 4-neck flask equipped with two addition funnels, pH electrode, thermometer and stir bar. 1.4 gms (0.035 mole) of NaOH and 2.4 gm (0.017 mole) of bromoacetic acid were each dissolved in 10 ml of deionized water and charged to the two addition funnels. Sufficient NaOH was added to the stirring diamine solution to bring the pH to about 11, which raised the temperature to about 40° C. The temperature was maintained at 40 C, and bromoacetic acid and NaOH were added concurrently to maintain the pH at 11 over the course of 3 hr. The reaction was monitored by HPLC. Dowex 50W-X8 resin was added to lower the pH from 11.1 to 3.1, the solution was filtered, and resin was washed with 100 ml of deionized water. The pH of the filtrate was about 3.3. 5 ml of 97% formic acid was added, and the pH dropped to 3.0. Then 10 ml of isopropyl alcohol was added with a few seed crystals, the product stirred overnight at 30° to 40° C., and then allowed to cool to 25° C. The crude product was collected by filtration and washed with deionized water. The crude product was then dried at 50° C. in vacuo to yield 3 gms of product (30% yield). The product can be recrystallized from a formic acid/water mixture to yield 2.4 gms in 96–98% purity by HPLC to yield N,N—bis-(pyridoxal-5-phosphate)ethylenediamine-N-acetic acid.

EXAMPLE 29

Other (Mono)acetic Acids

Repeating the procedure of Example 28 with the products of Examples 4, 14 and 15 yields the corresponding N,N'-bis(pyridoxal-5-phosphate)-1,3-(n-propylene)diamine-N-acetic acid,
N,N'-bis(pyridoxal-5-phosphate)-1,2-(n-propylene)diamine-N-acetic acid,
N,N'-bis(pyridoxal-5-phosphate)-1,2-isopropylenediamine-N-acetic acid,
N,N'-bis(pyridoxal-5-phosphate)-1,2-(n-butylene)diamine-N-acetic acid,
N,N'-bis(pyridoxal-5-phosphate)-1,4-(n-butylene)diamine-N-acetic acid,
N,N'-bis(pyridoxal-5-phosphate)-1,3-(n-butylene)diamine-N-acetic acid,
N,N'-bis(pyridoxal-5-phosphate)-1,2-(3-methyl)propylene-diamine-N-acetic acid,
N,N'-bis(pyridoxal-5-phosphate)-trans-1,2-cyclohexylene-diamine-N-acetic acid,
N,N'-bis(pyridoxal-5-phosphate)-trans-1,2-cyclopentylene-diamine-N-acetic acid,
N,N'-bis(pyridoxal-5-phosphate)-trans-1,2-cycloheptylene-diamine-N-acetic acid,
N,N'-bis(pyridoxal-5-phosphate)-trans-1,2-cyclooctylene-diamine-N-acetic acid,
N,N'-bis(pyridoxal-5-phosphate)-1,2-phenylenediamine-N-acetic acid, and
N,N'-bis(pyridoxal-5-phosphate)-cis-1,2-cyclohexylenediamine-N-acetic acid.

EXAMPLE 30

Other Chelates

Repeating the procedures of Example 26 but replacing the products of Example 29 for the product of Example 24 yields the $^{99m}$Tc, $^{95}$Tc, $^{99}$Tc, $^{51}$Cr(III), $^{57}$Co(II), $^{67}$Ga(III), $^{68}$Ga(III), $^{111}$In(III), $^{113m}$In(III), $^{197}$Hg(II), $^{75}$Se(IV), $^{201}$Tl(III), $^{203}$Pb(II), $^{85}$Sr(II), $^{87m}$Sr(II), $^{135m}$Sm(III), $^{153}$Sm(III), $^{171}$Er(III), $^{169}$Yb(III), $^{62}$Zn(II) and $^{186}$Re(III) radioactive metal ion chelates of the sodium-calcium salts of the monoacetic acid chelating agents of Example 29.

EXAMPLE 31

N-pyridoxal-N'-(pyridoxal-5-phosphate)-ethylenediimine

A 25 gm (0.123 mole) quantity of pyridoxal hydrochloride is slurried in 100 ml of methanol, and 4.88 gm (0.123 mole) of NaOH is added. When the solution is homogeneous, it is added dropwise to 7.5 gm of 1,2-diaminoethane in 100 ml of methanol with stirring. After 60 min, a methanol solution containing 32.7 gm (0.123 mole) of pyridoxal-5-phosphate and 4.88 gm (0.123 mole) is added with vigorous stirring. The unsymmetrical imine product, 5-(N-(3-hydroxy-5-hydroxymethyl-2-methyl-4-pyridyl)-methylideneaminoethyleneiminomethyl)-2-hydroxy-3-methyl-5-pyridylmethylphosphoric acid or N-pyridoxal-N,-(pyridoxal-5-phosphate)-ethylenediimine, is stirred for 1 hr, and the product is isolated by filtration. The diimine is washed with methanol (2×50 ml) and diethyl ether (2×50 ml), and dried in vacuo.

EXAMPLE 32

N-pyridoxal-N'-(pyridoxal-5-phosphate)-ethylenediamine

Repeating the procedure of Example 3 but substituting the diimine product of Example 31 for the diimine product of Example 1 yields the corresponding diamine product, 5-(N-(3-hydroxy-5-hydroxymethyl-2-methyl-4-pyridyl)-methylaminoethyleneaminomethyl)-2-hydroxy-3-methyl-5-pyridylmethylphosphoric acid or N-pyridoxal-N'-(pyridoxal-5-phosphate)-ethylenediamine.

EXAMPLE 33

DPMP Synthesis

Repeating the procedures of Example 5 and 6 with the product of Example 32 yields the corresponding N-pyridoxal-N'-(pyridoxal-5-phosphate)ethylenediamine-N,N'-diacetic acid or N-(3-hydroxy-5-hydroxyomethyl-2-methyl-4-pyridylmethyl)-N'-(3-hydroxy-2-methyl-5-phosphonomethyl-4-pyridyl-methyl)ethylenediamine-N,N'-diacetic acid (DPMP).

EXAMPLE 34

DPMP Chelates

Repeating the procedures of Example 26 but replacing the product of Example 33 for the product of Example 24 yields the $^{99m}$Tc, $^{95}$Tc, $^{99}$Tc, $^{51}$Cr(III), $^{57}$Co(II), $^{67}$Ga(III), $^{68}$Ga(III), $^{111}$In(III), $^{113m}$In(III), $^{197}$Hg(II), $^{75}$Se(IV), $^{201}$Tl(III), $^{203}$Pb(II), $^{85}$Sr(II), $^{87m}$Sr(II), $^{135m}$Sm(III), $^{153}$Sm(III), $^{171}$Er(III), $^{169}$Yb(III), $^{62}$Zn(II) and $^{186}$Re(III) radioactive metal ion chelates of the sodium-calcium salts of N-pyridoxal-N'-(pyridoxal-5-phosphate)ethylene-diamine-N,N'-diacetic acid.

We claim:

1. A radioactive metal ion chelate of the chelating compound of the formula:

(I)

wherein said compound is chelated with a radioactive metal iron, wherein

R is hydrogen or $R_1$ is hydrogen or and one of R and $R_1$ is other than hydrogen;
$R_3$ is alkylene having from 1 to 8 carbons, 1,2-cycloalkylene having from 5 to 8 carbons, or 1,2-arylene having from 6 to 10 carbons, or
$R_4$ is hydrogen, hydroxymethyl, alkyl having from 1 to 6 carbons or $R_5$ and $R_6$ are each, individually, hydroxy, alkoxy having from 1 to 18 carbons, hydroxy-substituted alkoxy having from 1 to 18 carbons, amino or alkylamido having from 1 to 18 carbons;
the phosphate group mono and diesters of the compounds thereof with monohydric and polyhydric alcohols having from 1 to 18 carbons, or alkylamino alcohols, each having from 1 to 18 carbons, and the salts thereof.

2. A radioactive metal ion chelate of a chelating compound of claim 1 wherein $R_3$ is alkylene having from 2 to 6 carbons.

3. A radioactive metal ion chelate of the chelating compound of claim 1 wherein R is and $R_1$ is 4. A radioactive metal ion chelate of the chelating compound of claim 3 wherein $R_5$ and $R_6$ are each, individually, hydroxy, alkoxy having from 1 to 8 carbons, amino or alkylamido having from 1 to 8 carbons.

5. A radioactive metal ion chelate of the chelating compound of claim 4 wherein $R_5$ and $R_6$ are hydroxy or a salt thereof.

6. As a radioactive metal ion chelate of a chelating compound of claim 5, a radioactive metal chelate of N,N'-bis-(pyridoxal-5-phosphate)ethylenediamine-N,N'-diacetic acid or a salt thereof.

7. A radioactive metal ion chelate of a chelating compound of claim 1 wherein $R_3$ is cyclohexyl.

8. As a radioactive metal ion chelate of a chelating compound of claim 7, a radioactive metal chelate of N,N'-bis-(pyridoxal-5-phosphate)-trans-1,2-cyclohexyldiamine-N,N'-diacetic acid or a salt thereof.

9. A radioactive metal ion chelate of claim 1, 2, 3, 4, 5, 6, 7, or 8 with a metal ion having a gamma emission between 20 and 600 KeV and a half-life between one hour and one year.

10. A radioactive metal ion chelate of claim 9 wherein the metal ion is selected from the group consisting of ions of $^{99m}Tc$, $^{99}Tc$, $^{95}Tc$, $^{51}Cr$, $^{57}Co$, $^{67}Ga$, $^{68}Ga$, $^{111}In$, $^{113m}In$, $^{197}Hg$, $^{75}Se$, $^{201}Tl$, $^{203}Pb$, $^{85}Sr$, $^{87m}Sr$, $^{135m}Sm$, $^{153}Sm$, $^{171}Er$, $^{169}Yb$, $^{62}Zn$, and $^{186}Re$.

11. A calcium salt of a chelate of claim 9.

12. A calcium salt of claim 11 wherein the molar ratio of calcium to chelating compound is from 0.05 to 1.0.

13. A calcium salt of claim 12 wherein the molar ratio of calcium to chelating compound is from 0.1 to 0.5.

14. A radioactive metal ion chelate of a compound of claim 1, 2, 3, 4, 5, 6, 7, or 8 with a technetium-99m metal ion.

15. As a chelate of claim 14, a technetium-99m chelate of N,N'-bis-(pyridoxal-5-phosphate)-trans-1,2-cyclohexyldiamine-N,N,-diacetic acid or a salt thereof.

16. As a chelate of claim 14, a technetium-99m chelate of N,N'-bis-(pyridoxal-5-phosphate)ethylenediamine-N,N'-diacetic acid or a salt thereof.

17. A calcium salt of the chelate of claim 15.

18. A calcium salt of claim 16 wherein the molar ratio of calcium to chelating compound is from 0.05 to 1.0.

19. A calcium salt of claim 17 wherein the molar ratio of calcium to chelating compound is from 0.1 to 0.5.

20. A radioactive metal ion imaging composition consisting essentially of a chelate of a radioactive metal ion chelate of a compound of claim 1, 2, 3, 4, 5, 6, 7 or 8 and a pharmaceutically acceptable, compatible excipient.

21. A radioactive metal ion imaging composition of claim 20 consisting essential of a chelate of a radioactive metal ion having a gamma emission between 20 and 600 KeV and a half-life between one hour and one year and a pharmaceutical acceptable, compatible excipient.

22. A radioactive metal ion imaging composition of claim 21 wherein the metal ion is selected from the group consisting of ions of $^{99m}Tc$, $^{99}Tc$, $^{95}Tc$, $^{51}Cr$, $^{57}Co$, $^{67}Ga$, $^{68}Ga$, $^{111}In$, $^{113m}In$, $^{197}Hg$, $^{75}Se$, $^{201}Tl$, $^{203}Pb$, $^{85}Sr$, $^{87m}Sr$, $^{135m}Sm$, $^{153}Sm$, $^{171}Er$, $^{169}Yb$, $^{62}Zn$, and $^{186}Re$.

23. A radioactive metal ion imaging composition of claim 22 wherein the metal ion is a technetium-99m ion.

24. A radioactive metal ion imaging composition of claim 21 containing a calcium salt of the chelate.

25. A radioactive metal ion imaging composition of claim 24 containing a calcium salt of the chelate wherein the molar ratio of calcium to chelating compound is from 0.05 to 1.0.

26. A radioactive metal ion imaging composition of claim 25 containing a calcium salt wherein the molar ratio of calcium to chelating compound is from 0.1 to 0.5.

27. A radioactive metal ion imaging composition of claim 21 wherein the compound is N,N'-bis-(pyridoxal-5-phosphate)ethylenediamine-N,N'-diacetic acid, N,N'- bis-(pyridoxal-5-phosphate)-trans-1,2-cyclohexyl diamine-N,N'-diacetic acid, or a salt thereof.

28. A radioactive metal ion imaging composition of claim 27 containing a calcium salt.

29. A radioactive metal ion imaging composition of claim 28 containing a calcium salt, wherein the molar ratio of calcium to chelating compound is from 0.05 to 1.0.

30. A radioactive metal ion imaging composition of claim 29 containing a calcium salt, wherein the molar ratio of calcium to chelating compound is from 0.1 to 0.5.

31. A radioactive metal ion imaging composition of claim 21 wherein the concentration of chelate salt in the medium is from 0.01 to 10 mCi per ml.

32. A radioactive metal ion imaging composition of claim 31 wherein the concentration of chelate salt in the medium is from 2 to 5 mCi per ml.

33. An improvement in the method of performing radiopharmaceutical imaging with a patient comprising administering to the patient, an effective amount of a radioactive metal ion chelate of claim 1, 2, 3, 4, 5, 6, 7 or 8.

34. An improvement in the method of performing radiopharmaceutical imaging of a patient of claim 33 wherein the radioactive metal ion has a gamma emission between 20 and 600 KeV and a half-life between one hour and one year.

35. An improvement in the method for performing radiopharmaceutical imaging of a patient of claim 34 wherein the metal ion is selected from the group consisting of ions of $^{99m}$Tc, $^{99}$Tc, $^{95}$Tc, $^{51}$Cr, $^{57}$Co, $^{67}$Ga, $^{68}$Ga, $^{111}$In, $^{113m}$In, $^{197}$Hg, $^{75}$Se, $^{201}$Tl, $^{203}$Pb, $^{85}$Sr, $^{87m}$Sr, $^{135m}$Sm, $^{153}$Sm, $^{171}$Er, $^{169}$Yb, $^{62}$Zn, and $^{186}$Re.

36. An improvement in the method for performing radiopharmaceutical imaging of claim 34 wherein the metal ion is a technetium-99m ion.

37. An improvement in the method for performing radiopharmaceutical imaging of claim 34 wherein the compound is
N,N'-bis-(pyroxidal-5-phosphate)ethylenediamine-N,N'-diacetic acid,
N,N'-bis-(pyridoxyl-5-phosphate)-trans-1,2-cyclohexyldiamine-N,N'-diacetic acid, or a salt thereof.

38. An improvement in the method for performing radiopharmaceutical imaging of claim 34 wherein the chelate of the compound is a calcium salt.

39. An improvement in the method for performing radiopharmaceutical imaging of claim 38 wherein the molar ratio of calcium to chelate is from 0.05 to 1.0.

40. An improvement in the method for performing radiopharmaceutical imaging of claim 39 wherein the molar ratio of calcium to chelate is from 0.1 to 0.5.

41. An improvement in the method for performing radiopharmaceutical imaging of claim 34 wherein the metal ion is technetium-99m and the compound is
N,N'-bis-(phyidoxal-5-phosphate)ethylenediamine-N,N'-diacetic acid,
N,N'-bis-(phridoxyl-5-phosphate)-trans-1,2-cyclohexyldiamine-N,N'-diacetic acid, or a salt thereof.

42. An improvement in the method for performing radiopharmaceutical imaging of claim 41 wherein the salt is a calcium salt with a molar ratio of calcium to chelating compound of from 0.05 to 1.0.

43. An improvement in the method of performing radiopharmaceutical imaging of claim 33 wherein from 0.001 to 1 mCi of chelate is administered per kg of patient body weight.

44. An improvement in the method of performing radiopharmaceutical imaging of claim 43 wherein from 0.002 to 0.1 mCi of chelate is administered per kg of patient body weight.

* * * * *